United States Patent [19]
Chen et al.

[11] Patent Number: 5,434,325
[45] Date of Patent: Jul. 18, 1995

[54] PROCESS FOR THE PRODUCTION OF TERTIARY BUTYLETHYLBENZENE

[75] Inventors: Shiou-Shan Chen, Winchester; Joseph C. Peters, Quincy, both of Mass.

[73] Assignee: Deltech Corporation, Whippany, N.J.

[21] Appl. No.: 277,787

[22] Filed: Jul. 20, 1994

Related U.S. Application Data

[63] Continuation of Ser. No. 80,878, Jun. 21, 1993, abandoned.

[51] Int. Cl.$^6$ ............................................. C07C 2/66
[52] U.S. Cl. ..................... 585/448; 585/315; 585/316; 585/323; 585/446; 585/449
[58] Field of Search ............... 585/315, 316, 323, 448, 585/449

[56] References Cited

U.S. PATENT DOCUMENTS

| | | | |
|---|---|---|---|
| 2,360,358 | 10/1944 | Mattox | 585/316 |
| 2,904,607 | 9/1959 | Mattox et al. | 260/671 |
| 3,251,897 | 5/1966 | Wise | 260/671 |
| 3,631,120 | 12/1971 | Eberly, Jr. et al. | 260/671 |
| 3,641,177 | 2/1972 | Eberly, Jr. et al. | 260/671 |
| 3,755,483 | 8/1973 | Burress | 260/671 |
| 3,766,290 | 10/1973 | Carlson | 260/672 |
| 3,772,398 | 11/1973 | Carr et al. | 260/671 |
| 3,776,971 | 12/1973 | Carr et al. | 260/671 |
| 4,008,290 | 2/1977 | Ward | 260/672 |
| 4,169,111 | 9/1979 | Wight | 585/323 |
| 4,795,550 | 1/1989 | Sachtler et al. | 208/307 |
| 4,849,569 | 7/1989 | Smith, Jr. | 585/446 |
| 4,922,053 | 5/1990 | Waguespack et al. | 585/449 |
| 5,012,021 | 4/1991 | Vora et al. | 585/315 |
| 5,073,653 | 12/1991 | Butler | 585/449 |
| 5,105,041 | 4/1992 | Ferk et al. | 584/450 |
| 5,215,725 | 6/1993 | Sy | 422/212 |
| 5,243,115 | 9/1993 | Smith et al. | 585/446 |

*Primary Examiner*—Asok Pal
*Attorney, Agent, or Firm*—Perman & Green

[57] ABSTRACT

The present invention provides an alkylation process which is highly selective towards the production of para-tertiarybutylethylbenzene in high yield and in high para isomer content, while minimizing the development of unwanted by-products and impurities during the alkylation reaction. In accordance with the process, a feed stream mixture comprising the olefin alkylating agent and a molar excess of an aromatic hydrocarbon substrate is introduced into the inlet of a reactor zone and through a bed of active zeolite alkylation catalyst under alkylation conditions such that substantially all of the olefin reacts with the aromatic substrate to produce a mixture comprising the alkylated product and unreacted aromatic compound. This mixture is continuously withdrawn from the reactor zone as reactor effluent, after which the effluent is split into a product stream and recycle stream. The recycle stream is continuously recirculated back into the inlet of said reactor zone, preferably after being first combined with fresh feed stream mixture, in an amount such that the quantity of said aromatic compound and said olefin present in said reaction zone prior to contact with said catalyst is maintained at a preferred mole ratio greater than 10 to 1.

19 Claims, 1 Drawing Sheet

PROCESS FOR THE PRODUCTION OF TERTIARY BUTYLETHYLBENZENE

This is a continuation of application Ser. No. 08/080,878 filed on Jun. 21, 1993, abandoned.

BACKGROUND OF THE INVENTION

Field of the Invention

The present invention relates to an improved process for the monoalkylation of ethylbenzene with isobutene or the monoalkylation of isobutylbenzene with ethylene to form tertiarybutylethylbenzene of high purity, and which process is highly selective towards production of the para isomer.

Description of Related Art Para-tertiarybutylstyrene (Para TBS) is a well known monomeric material useful in the preparation of polymers and copolymers which are in turn useful as ingredients in paint and coating compositions, as well as in the production of thermoset resins.

Para-TBS is produced by the dehydrogenation of the para-tertiarybutylethylbenzene (para TBEB) precursor material using conventional dehydrogenation techniques. Para TBEB is itself most commonly produced by the alkylation of ethylbenzene with isobutene in the presence of an alkylation catalyst.

Mixed meta and para TBEB may be typically prepared by the catalytic alkylation of ethyl benzene with isobutylene in the presence of a Friedel-Crafts type catalyst such as sulfuric acid, $BF_3$, aluminum trichloride, liquid hydrofluoric acid as well as mixtures thereof, such as disclosed in U.S. Pat. Nos. 3,631,213 and 4,982,034.

Whereas these processes produce TBEB in relatively good yields, they generally give rise to a mixture of the para and meta isomers of TBEB which are difficult to separate out because of their relatively close boiling points. The most valuable and useful isomer is the para isomer since its dehydrogenation product (para TBS) is the most desired monomer for use in the polymer applications described above.

Crystalline aluminosilicate catalysts, or zeolite catalysts, are also known to be useful to catalyze the alkylation of aromatic compounds using olefins as the alkylation agent. For example, U.S. Pat. No. 4,469,908 discloses the alkylation of aromatic hydrocarbons by contacting a mixture of aromatic hydrocarbon and a lower olefin, present in a mole ratio in the range of 20/1 to 1/1 respectively, with a crystalline zeolite catalyst at a temperature of between 100° C. and 300° C. and under sufficient pressure to maintain the organic reactants in the liquid phase. The alkylation of ethylbenzene with isobutylene using the acid form of ZSM-12 Zeolite is particularly disclosed wherein greater than 95% conversion of isobutylene is achieved with a selectivity of 90% towards para TBEB and 10% towards meta TBEB.

In spite of the availability of highly selective zeolite catalysts which are active for these alkylations, the production of alkylated aromatic compounds frequently suffers from undesirable side reactions which cause the formation of unwanted isomers and impurities. For example, exposure of a reaction stream which includes isobutene and ethylbenzene to conditions of temperature and pressure sufficient to induce catalytic alkylation with high product yield may cause some cracking and isomerization of the reaction product as well as undesired isobutene oligomerization, and the formation of some of the unwanted trialkyl isomers of TBEB.

It is generally known in the art that the quantity of unwanted polyalkyl benzene by-products produced during monoalkylation can be minimized by conducting the alkylation using relatively high molar ratios of aromatic substrate to alkylating agent and/or by separating the unwanted polyalkylaromatics from the monoalkylation product and recirculating the former back to the reactor to undergo transalkylation.

In one particular embodiment of an alkylation process, a mixture of olefin, e.g. ethylene, aromatic substrate, e.g., benzene, and catalyst, e.g., aluminum chloride, are pumped into a tank reactor, mixed and subjected to conditions of temperature and pressure sufficient to cause alkylation of the aromatic substrate with the olefin. A portion of the reaction mixture containing the reaction product, unreacted aromatic substrate, some unreacted olefin and catalyst is continuously withdrawn from the reactor, cooled, mixed with fresh ethylene and benzene, and pumped back into the reactor as a method of controlling the temperature of the exothermic reaction in the reactor and enhancing mixing of the reactants. However, this process suffers the disadvantage of the need to neutralize, remove and dispose of the aluminum chloride catalyst as well as the difficulty in controlling precisely the olefin to aromatic substrate molar ratios throughout the reaction mass.

U.S. Pat. No. 3,766,290 discloses a process for preparing alkylated aromatics comprising contacting a mixture of alkylating agent, aromatic hydrocarbon and polyalkylated aromatic hydrocarbon with an alkylation catalyst in a reactor vessel under alkylation conditions, separating the crude reaction product from the catalyst, separating the alkylated aromatic hydrocarbon from the unconverted aromatic hydrocarbon, further separating the monoalkylated aromatic hydrocarbon from the polyalkylated aromatic hydrocarbon and recycling the aromatic hydrocarbon and polyalkylated aromatic hydrocarbon back to the reactor vessel.

U.S. Pat. No. 4,169,111 discloses a process for the manufacture of ethylbenzene wherein a mixture of ethylene and excess benzene is contacted with an alkylation catalyst in a reactor to produce a product comprising a mixture of ethylbenzene, diethylbenzene and triethylbenzene, separating the product into benzene and each of the alkyl and polyalkylbenzene fractions, and recycling at least a portion of the separated diethylbenzene fraction back to the reactor.

The prior art also discloses several techniques for conducting alkylation reactions where high molar ratios of aromatic substrate to alkylating agent are achieved. For example, U.S. Pat. No. 4,849,569 teaches that enhanced selectively towards the production of monoalkylbenzenes can be achieved by providing a mole ratio of benzene to olefin alkylating agent in the ratio of 2 to 100 : 1, more preferably from about 2 to 10 : 1. However, a major disadvantage of this process involves the separation and recovery of large volumes of unreacted aromatic hydrocarbon which lends inefficiency and increased cost to the process.

Another technique to obtain the advantages of the use of relatively high aromatic substrate/alkylating agent mole ratios is to conduct the alkylation process in a multibed, multistage reactor wherein only a portion of the total moles of alkylating agent is injected at each stage of the reactor as the reaction stream passes through the reactor. Examples of such techniques are disclosed in U.S. Pat. Nos. 4,922,053 and 5,073,653. However, the use of such systems requires more elaborate process temperature control and catalyst handling procedures in order to avoid catalyst deactivation caused by rapid build up of coke on the catalyst surface.

SUMMARY OF THE INVENTION

The present invention provides an alkylation process which is highly selective towards the production of para TBEB in high yield and in high para isomer content, while minimizing the development of unwanted by-products and impurities during the alkylation reaction. In accordance with the process, a feed stream mixture comprising the olefin alkylating agent and a molar excess of an aromatic hydrocarbon substrate is introduced into the inlet of a reactor zone and through a bed of active zeolite alkylation catalyst under alkylation conditions such that substantially all of the olefin reacts with the aromatic substrate to produce a mixture comprising the alkylated product and unreacted aromatic compound. This mixture is continuously withdrawn from the reactor zone as reactor effluent, after which the effluent is split into a product stream and recycle stream. The recycle stream is continuously recirculated back into the inlet of said reactor zone, preferably after being first combined with fresh feed stream mixture, in an amount such that the quantity of said aromatic compound and said olefin present in said reaction zone prior to contact with said catalyst is maintained at a preferred mole ratio greater than 10 to 1.

The process provides a number of additional advantages over conventional alkylation processes, including the benefits derived from the utilization of a large stoichiometric excess of aromatic reactant during alkylation without the concomitant generation of large volumes of unreacted aromatics which must be separated. The process also allows for the utilization of a single catalyst bed in the reactor zone which offers more facile control of the temperature of the exothermal alkylation reaction and control of coke build up on the catalyst than where multiple catalyst bed reactors are employed. Another advantage of the process is that it allows for more precise control of both alkylation reactor temperature and the stoichiometric ratio of olefin and aromatic substrate present in the reactor prior to contact with the catalyst bed.

BRIEF DESCRIPTION OF THE DRAWING

The FIGURE is a schematic representation of a preferred embodiment of the process and system of the invention.

DETAILED DESCRIPTION OF THE INVENTION

Figure 1:
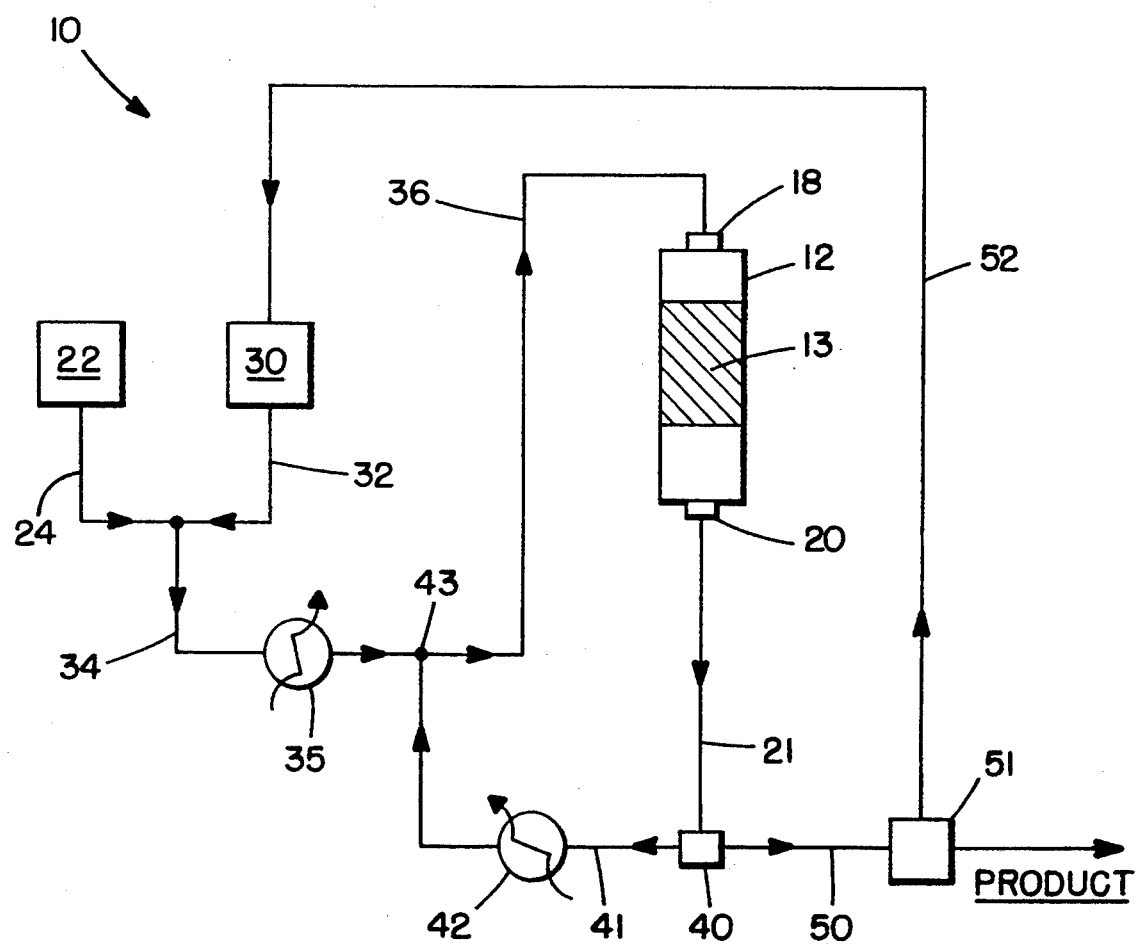

The preferred product which is prepared in accordance with the invention is tertiarybutylethylbenzene (TBEB) preferably containing at least 90% by weight, more preferably containing at least 95% by weight of the para isomer. This product can be obtained by two different synthesis routes: (a) isobutylation of an monoethylbenzene substrate or (b) ethylation of a mono-isobutylbenzene substrate. The more preferred route for the purposes of this invention is isobutylation of the mono-ethylbenzene substrate because it permits liquid phase alkylation at lower pressures and also provides for greater selectivity towards formation of the para isomer.

One illustration of the preferred mode of this invention is shown in the FIGURE. The aromatic alkylation system 10 includes vertical reactor 12 packed with catalyst 13. Reactor 12 is suitable for exposing a reaction stream comprising a mixture of alkylating agent, e.g. isobutene, and a molar excess of aromatic hydrocarbon substrate, e.g., ethylbenzene to conditions of temperature and pressure sufficient such that substantially all of the isobutene reacts with the ethylbenzene substrate, leaving a post-alkylation reactor effluent comprising a mixture of TBEB and unreacted ethylbenzene. By the term "substantially all" is meant that at least 90% by weight, more preferably at least 99% by weight of the isobutene introduced into the reactor at inlet 18 is consumed in the alkylation reaction leaving only minor to trace amounts of unconverted isobutene in the effluent as it exits at reactor discharge 20.

The reactor flow shown in the FIGURE is in the down mode, but the reactor may be configured for flow in either the down, radial, up or horizontal mode. A wide variety of reactors can be employed such as fixed or moving bed reactors which may contain single or multiple catalyst beds. The preferred reactor is a single bed reactor wherein greater than 50% of the volume is packed with a single catalyst bed.

The preferred catalyst materials used in the present invention are synthetic crystalline aluminosilicates which are referred to as zeolites. The class of zeolites which may be used are those which are active for the target alkylation product and may include materials such as ZSM-5, ZSM-12, zeolite beta and other zeolites such as disclosed in U.S. Pat. No. 4,469,908, the complete disclosure of which is incorporated herein by reference. The most preferred zeolite is the acid or hydrogen form of ZSM-12 because it is very active in the liquid phase alkylation of ethylbenzene with isobutene and gives high yields and selectivity toward the production of para TBEB.

Zeolite ZSM-12 is a known synthetic crystalline aluminosilicate which is described in U.S. Pat. Nos. 3,832,449 and 3,970,544, the entire disclosures of which are incorporated herein by reference.

For high catalytic activity, the zeolite should be predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, a major portion of the cation sites are occupied by hydrogen ions. It is especially preferred that at least about 80% of the cation sites are occupied by hydrogen ions.

The pure zeolite per se may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 wt.% of the zeolite. Usually the zeolite content will range from 10 to 90 wt.% and more typically from 60 to 80 wt.%. The preferred inorganic binder is alumina. The mixture may be formed into tablets or extrudates having the desired shape by extrusion methods well known in the art. The extrudates or tablets will usually be cylindrical in shape. Other shapes with enhanced surface-to-volume ratios, such as fluted or polylobed cylinders, can be employed to enhance mass transfer rates and, thus, catalytic activity.

Turning once again to the FIGURE, an initial feed stream mixture is formed by directing a suitable alkylating agent e.g., isobutene, from isobutene source 22 through line 24 and a suitable aromatic hydrocarbon, e.g. ethylbenzene, from ethylbenzene source 30 through line 32 and combining these initial streams in line 34 to produce a feed stream mixture. The feed ratio of these reactants is set such that the ethylbenzene is present in the feed stream mixture at a molar excess, generally in the range of greater than 1 to 1 up to less than about 20 to 1 molar excess with respect to isobutene. The preferred mole ratio of ethylbenzene to isobutene at this point in the process lies in the range of about 3 to 15 moles of ethylbenzene per mole of isobutene, more preferably less than 10 moles of ethylbenzene per mole of isobutene.

The feed stream is thereafter directed via lines 34 and 36 through reactor inlet 18 and into reactor 12. Heat exchanger 35 is provided to heat the feed stream as necessary to a temperature approaching alkylation temperature and/or to balance the temperature of feed stream to accommodate the temperature of the recycle stream a hereinafter discussed. Typical temperatures of the feed stream at feed stream inlet 18 will be in the range of between about 200° and 500° F., and preferably in the range of between about 250° and 350° F. However, the optimal temperature will be specific to the reactants, catalyst and other operating parameters.

The feed stream is exposed to the catalyst in reactor 12 under conditions of pressure and temperature sufficient to provide liquid phase alkylation and such that substantially all of the iosbutene reacts with ethylbenzene to form TBEB, resulting in an effluent composed primarily of a mixture comprising TBEB and unreacted ethylbenzene. Preferred reaction pressures within the reactor system lie in the range of about 50 to 1000 psig respectively, more preferably from 100 to 600 psig.

The effluent is directed out of the reactor through reactor outlet 20 and through line 21 after which the effluent is split at point 40 to form a recycle stream and a product stream. The recycle stream is directed in total back into reactor 12 through inlet 18 where it is combined and mixed with the initial feed stream prior to contact with catalyst 13. In the preferred mode of the FIGURE, the recycle stream is recirculated via line 41 and first combined with the initial feed stream at mixing point 43, and this mixture is then directed via line 36 to reactor zone inlet 18. A suitable heat exchanger 42 is positioned in line 41 to cool the recycle stream such that, when it is combined with the initial feed stream, the temperature of the feed stream at reactor inlet 18 is controlled and maintained at a point within the preferred range of 250° to 350° F.

The effluent directed from the reactor is split or proportioned so that the amount of recycle recirculated into the reactor is sufficient such that the quantity of unreacted ethylbenzene and isobutene introduced into the reactor prior to contact with the catalyst is maintained at a mole ratio of greater than 10 to 1, preferably greater than 20 to 1, more preferably greater than 50 to 1, even more preferably greater than 75 to 1 and most preferably greater than 100 to 1 respectively. To achieve these ratios, at least 50% by weight of the effluent from line 21 is directed as recycle through line 41 and more preferably at least about 75% by weight of the effluent is so directed, with the balance of the effluent directed via line 50 to product recovery. In a particularly preferred embodiment of the invention, approximately 90 to 95% by weight of the effluent is recycled and the balance of the effluent sent to product recovery for further processing. In accordance with this process, the molar ratio of ethylbenzene to isobutene will always be higher after the recycle stream and initial feed stream are combined than the molar ratio of ethylbenzene to isobutene in the initial feed stream, generally at least twice as high and preferably at least ten times as high.

The product stream is discharged via line 50, cooled and directed into separator 51 wherein unreacted aromatic hydrocarbon, e.g. ethylbenzene, is separated from the alkylated product, e.g. TBEB. Separation may be accomplished by conventional techniques such as distillation, membrane separation and the like, after which the ethylbenzene may be recycled to ethylbenzene source 30 via line 52 for re-use in the process.

It is to be emphasized that the key factor in achieving the advantage of this invention is control of the relative mole ratio of unreacted ethylbenze to isobutene just prior to contact with the catalyst at the levels set forth above. Thus, the invention is not limited to the preferred embodiment wherein the fresh isobutene 22 and fresh ethyl benzene 30 are first combined and this mixture is then combined with the recycle stream prior to catalyst contact. For example, isobutene, fresh ethylbenzene and the recycle stream can be introduced into the reactor via separate lines, or the recycle stream can be combined with either isobutene or fresh ethylbenzene, with the non-combined component being subsequently combined with these mixtures or introduce separately into the reactor.

Typical temperatures of the feed stream at reactor inlet 18 will range from about 200° to 500° F., preferably from about 250° to 350° F. and the temperature of the effluent as it exits reactor outlet 20 will range from about 4° to about 20° F. higher due to exothermic nature of the alkylation reaction.

In a particularly preferred embodiment of the invention, ethylbenzene and isobutene are combined in line 34 at a respective mole ratio of about 7 to 1 and the mixture preheated to about 265° F. at heat exchanger 35. Effluent emerging from the reactor at about 316° F. is split at a ratio of about 92 to 94% by weight recycle stream and about 6 to about 8% by weight product stream, and the recycle stream is cooled such that the temperature of the combined initial feed stream and recycle stream is about 310° F. as it enters the reactor at reactor inlet 18. Operation in this mode provides for an ethylbenzene/isobutene mole ratio in the reactor, prior to contact with catalyst, slightly in excess of 100 to 1 respectively. Preferred pressures in this mode range from 100 to 600 psig.

Contact time within the reactor generally ranges from about 10 seconds to 10 hours, but is normally from 5 minutes to about 1 hour depending upon reactor configuration. The weight hourly space velocity (WHSV) in terms of weight of reactants per unit weight of catalyst per hour is generally within the range of about 0.5 to 50, more preferably from about 2.5 to about 20 with respect to the net or fresh feed of the ethylbenzene and isobutene, and from about 5 to 400, more preferably from about 25 to 200 with respect to the gross reactor feed after the fresh feed stream and recirculating recycle streams are combined.

Conducting the alkylation process of this invention wherein a portion of the effluent from the reactor is recirculated back into the reactor feed stream thus provides an efficient and cost effective method for obtaining reaction specificity of alkylation as a consequence of very dilute alkylating agent/aromatic substrate molar ratios and a more precise technique for control of reaction temperatures and the molar ratio of reactants, thereby significantly reducing ancillary side reactions which produce undesirable and unwanted reaction products such as those caused by polyalkylation, oligomerization, cracking and isomerization of the reactants or desired reaction product. In addition, because the bulk of the aromatic substrate remains captive in the alkylation feed stream, separation of the aromatic substrate from the alkylated product and recycle of the aromatic substrate are greatly simplified.

The advantages of the process of this invention are illustrated by the following examples.

EXAMPLE 1 (COMPARATIVE)

In this example, TBEB was produced by passing a mixture of ethylbenzene and isobutene once through a 41" long, 0.5" diameter tubular pipe reactor packed with a bed of the hydrogen form of ZSM-12 catalyst pellets. Runs A and B were conducted using 25 grams of catalyst. In both runs, the feed to the reactor was preheated to reaction temperature before entering the catalyst bed and reaction temperature was maintained using electrical elements around the reactor. Reaction conditions, weight hourly space velocity (WHSV)% isobutene, mole ratios of ethylbenzene (EB) to isobutene, product selectivity and isomer distribution in % by weight for each run are shown in Table I.

TABLE I

| Once-through Alkylation | | |
|---|---|---|
| Run | A | B |
| EB/isobutene mole ratio, net feed | 26 | 10 |
| WHSV isobutene feed | 0.5 | 0.5 |
| Temp, °F. | 319 | 314 |
| Press, psig | 451 | 450 |
| Selectivity, % | | |
| Oligomers | 2.7 | 2.5 |
| TBEB | 90.5 | 86.6 |
| Heavies | 5.9 | 10.2 |
| Others | 0.9 | 0.7 |
| Isomer Dist., % | | |
| meta-TBEB | 2.9 | 3.4 |
| para-TBEB | 97.1 | 96.6 |

As shown in Table I, the selectivity of the once-through process towards the production of TBEB was only 90.5%, even where a relatively high EB/isobutene mole ratio was evident as in Run A. The selectivity towards TBEB decreased by almost 4% to 86.6% in Run B at an EB/isobutene mole ratio of 10.

EXAMPLE 2

In this example, TBEB was produced in accordance with this invention wherein the reactor effluent was split and a portion of the effluent recycled and mixed with the fresh feed for recirculation in the reactor in accordance with the reaction schematic shown in the FIGURE. The reactor used in this example was a 24" long, 0.75" diameter tubular pipe reactor packed with a 30 gram bed of the hydrogen form of ZSM-12 catalyst pellets. A series of runs C–H were conducted under different reaction conditions. Reaction conditions, mole ratio of EB to isobutene, WHSV for fresh isobutene feed (net feed), the ratio of effluent recycle to fresh EB, selectivity and isomer distribution for each run are shown in Table II.

TABLE II

| | Alkylation With Effluent Recirculation | | | | | |
|---|---|---|---|---|---|---|
| Run | C | D | E | F | G | H |
| EB/isobutene mole ratio, net feed | 8 | 8 | 8 | 8 | 4 | 3 |
| WHSV isobutene feed | 0.5 | 0.5 | 0.5 | 0.5 | 0.5 | 0.5 |
| Recycle/fresh EB wt. ratio | 7 | 14 | 14 | 14 | 28 | 56 |
| Temp, °F. | 297 | 295 | 311 | 311 | 311 | 311 |
| Press, psig | 400 | 400 | 200 | 100 | 200 | 200 |
| Selectivity, % | | | | | | |
| Oligomers | 1.0 | 0.8 | 1.7 | 1.1 | 1.0 | 1.8 |
| TBEB | 94.4 | 96.2 | 95.2 | 95.6 | 94.8 | 92.5 |
| Heavies | 4.2 | 2.7 | 2.8 | 3.0 | 3.8 | 5.4 |
| Others | 0.4 | 0.3 | 0.3 | 0.3 | 0.3 | 0.3 |
| Isomer Dist., % | | | | | | |
| meta-TBEB | 4.3 | 3.3 | 3.3 | 3.6 | 4.5 | 4.1 |
| para-TBEB | 95.7 | 96.7 | 96.7 | 96.4 | 95.5 | 95.9 |

Run C in Table II shows that with a net EB/isobutene mole ratio of 8 and with effluent circulation, a selectivity of 94.4% to TBEB was achieved. When the effluent recycle/fresh EB weight ratio was increased from 7 in run C to 14 in runs D, E and F, the selectivity to TBEB further increased to the 95.2 to 96.2% range. Runs D, E and F also show that the selectivity to TBEB was relatively insensitive to the pressure. Run G shows that a selectivity to TBEB of nearly 95% was achieved at a low net EB/isobutene mole ratio of 4. Run H shows a selectivity to TBEB of 92.5% at a very low net EB/isobutene ratio of 3, which still compares favorably against Run A in Table 1 in which a selectivity to TBEB of 90.5% was obtained at a very high net EB/isobutene mole ratio of 28, but without effluent recycle.

What is claimed is:

1. A continuous process for the production of tertiarybutylethylbenzene comprising:
   a. continuously passing a feed stream comprising a mixture of isobutene with a molar excess of ethylbenzene into a reactor zone and through a bed of alkylation catalyst under alkylation conditions such that substantially all of said isobutene reacts with said ethylbenzene;
   b. continuously withdrawing an effluent from said reactor zone, said effluent comprising a mixture of tertiarybutylethylbenzene and unreacted ethylbenzene;
   c. splitting said effluent into a product stream and a recycle stream; and
   d. continuously recirculating said recycle stream directly back into said reactor zone in an amount such that the quantity of said ethylbenzene and said isobutene present in said reactor zone prior to contact with said catalyst is maintained at a mole ratio of greater than 10 to 1 respectively.

2. The process of claim 1 wherein the amount of said recycle stream recirculated to said reactor zone is sufficient to maintain a mole ratio of ethylbenzene to isobutene in said reactor zone prior to contact with said catalyst of greater than 20 to 1.

3. The process of claim 2 wherein said mole ratio is greater than 50 to 1.

4. The process of claim 2 wherein said mole ratio is greater than 100 to 1.

5. The process of claim 2 wherein said alkylation is conducted in the liquid phase.

6. The process of claim 5 wherein said recycle stream constitutes at least 50% by weight of said effluent.

7. The process of claim 6 wherein said recycle stream constitutes at least 75% by weight of said effluent.

8. The process of claim 6 wherein said recycle stream is first combined with said feed stream mixture prior to passing the mixture into said reactor zone.

9. The process of claim 6 wherein the unreacted ethylbenzene present in said product stream is separated from said alkylation product and recycled back to said feed stream mixture.

10. The process of claim 8 wherein the mole ratio of ethylbenzene to isobutene in said feed stream mixture prior to contact with said recycle stream is less than 20 to 1 and the mole ratio of ethylbenzene to isobutene in said feed stream after contact with said recycle stream is greater than 50 to 1.

11. The process of claim 10 wherein said mole ratio in said feed stream is from about 3 to about 15 to 1 and said mole ratio after contact with said recycle stream is greater than about 50 to 1.

12. The process of claim 6 wherein said alkylation catalyst is ZSM-12.

13. The process of claim 12 wherein a major portion of the cation sites in said ZSM-12 catalyst are occupied by hydrogen ions.

14. The process of claim 12 wherein the alkylation reaction is conducted at a temperature within the range of about 200° to 500° F. and a pressure within the range of about 50 to 1000 psig.

15. The process of claim 14 wherein said temperature is in the range of about 250° to 350° F. and said pressure is in the range of about 100 to 600 psig.

16. The process of claim 12 wherein the tertiarybutylethylbenzene reaction product comprises at least 90% by weight of the para isomer.

17. The process of claim 16 wherein said tertiarybutylethylbenzene reaction product comprises at least about 95% by weight of the para isomer.

18. The process of claim 6 wherein said recycle stream is cooled prior to recirculation back into said reactor zone.

19. The process of claim 9 wherein said recycle stream is cooled sufficient to reduce the temperature of said stream by from about 4° F. to about 20° F.

* * * * *